United States Patent
Verma

(10) Patent No.: US 9,103,586 B2
(45) Date of Patent: Aug. 11, 2015

(54) ADVANCED C2-SPLITTER FEED RECTIFIER

(75) Inventor: Vijender Kumar Verma, Sugar Land, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 2425 days.

(21) Appl. No.: 11/639,909

(22) Filed: Dec. 16, 2006

(65) Prior Publication Data

US 2008/0141713 A1 Jun. 19, 2008

(51) Int. Cl.
- F25J 3/00 (2006.01)
- F25J 3/02 (2006.01)
- C07C 7/00 (2006.01)
- C07C 11/02 (2006.01)
- C07C 11/24 (2006.01)

(52) U.S. Cl.
CPC ............... *F25J 3/0219* (2013.01); *C07C 7/005* (2013.01); *C07C 11/02* (2013.01); *C07C 11/24* (2013.01); *F25J 3/0233* (2013.01); *F25J 3/0238* (2013.01); *F25J 3/0242* (2013.01); *F25J 2200/74* (2013.01); *F25J 2200/78* (2013.01); *F25J 2215/62* (2013.01); *F25J 2270/90* (2013.01); *F25J 2290/80* (2013.01)

(58) Field of Classification Search
USPC .................... 62/617–620, 630, 631
See application file for complete search history.

(56) References Cited

U.S. PATENT DOCUMENTS

| | | | | |
|---|---|---|---|---|
| 2,813,920 | A | * | 11/1957 | Cobb, Jr. ................. 585/256 |
| 3,218,816 | A | * | 11/1965 | Grenier ..................... 62/630 |
| 4,312,652 | A | * | 1/1982 | Mikulla .................... 62/625 |
| 4,368,061 | A | * | 1/1983 | Mestrallet et al. .......... 62/630 |
| 4,452,281 | A | | 6/1984 | Speich |
| 4,900,347 | A | * | 2/1990 | McCue et al. ............. 62/627 |
| 5,372,009 | A | * | 12/1994 | Kaufman et al. ........... 62/630 |
| 5,421,167 | A | | 6/1995 | Verma |
| 5,453,559 | A | | 9/1995 | Phillips et al. |
| 5,678,424 | A | | 10/1997 | Nazar |
| 5,709,780 | A | | 1/1998 | Ognisty |
| 5,755,933 | A | | 5/1998 | Ognisty |
| 5,884,504 | A | | 3/1999 | Nazar |
| 6,021,647 | A | | 2/2000 | Ameringer et al. |
| 6,077,985 | A | | 6/2000 | Stork |
| 6,405,561 | B1 | | 6/2002 | Mortko et al. |
| 6,516,631 | B1 | | 2/2003 | Trebble |
| 6,601,406 | B1 | | 8/2003 | Deng et al. |

* cited by examiner

*Primary Examiner* — Ljiljana Ciric
*Assistant Examiner* — Alexis Cox
(74) *Attorney, Agent, or Firm* — Gary M. Machetta

(57) ABSTRACT

Processes to separate a light hydrocarbon stream comprising ethylene, ethane, and C3+ hydrocarbons into an ethylene stream, an ethane stream, and a C3+ hydrocarbon stream, including: feeding the light hydrocarbon stream to a deethanizer; separating the light hydrocarbons in the deethanizer to form a C3+ hydrocarbon bottoms stream and a C2-rich overhead stream comprising ethylene and ethane; separating the C2-rich stream in a C2-rectifier to form a first ethylene stream and an ethane-rich bottoms stream; and separating the ethane-rich bottoms stream in a C2-splitter to form a second ethylene stream and an ethane stream.

18 Claims, 3 Drawing Sheets

ADVANCED C2-SPLITTER FEED RECTIFIER

CROSS REFERENCE TO RELATED APPLICATIONS

1. Field

The embodiments relate generally to the separation of ethylene from ethane and more particularly to ethylene-ethane separation with an increased capacity of a C2-splitter.

2. Background

Ethylene is a building block in the manufacturing of a wide variety of chemical materials and is typically produced industrially by pyrolysis of hydrocarbons in a furnace in the presence of steam. The furnace effluent stream comprising a range of components is typically cleaned up, dried to remove water, compressed and passed to an olefins recovery section to separate the ethylene from other light hydrocarbons, such as ethane, propylene, propane, and the like.

The order of separation of compounds from the furnace effluent can begin with a demethanizer, deethanizer, or a depropanizer. For example, in a demethanizer-first fractionation process, effluent from a cracking furnace can be cooled and compressed and fed to the demethanizer, which removes methane and lighter compounds. The remainder of the furnace effluent leaves the bottom of the demethanizer and is supplied to a deethanizer.

The deethanizer separates the demethanizer bottoms effluent into C2s and lighter compounds which exit the overhead of the deethanizer as vapor and a portion containing heavier compounds which exits as deethanizer bottoms. The deethanizer bottoms are processed to separate the heavier components. The overhead C2s can be processed through a reactor to convert any acetylene to ethane and ethylene, or alternatively the acetylene can be separated from the ethane and ethylene in an acetylene recovery unit. The reactor or separator effluent can then be fed to a C2-splitter to separate the ethylene and ethane.

As improvements or expansions are made to the pyrolysis and other upstream processes, a need exists to improve the capacity of the downstream separation equipment, including improving the capacity of the C2-splitter. The method to increase the capacity of the C2-splitter should not compromise the quality of the separation achieved by the existing separation equipment.

BRIEF DESCRIPTION OF THE DRAWINGS

The detailed description will be better understood in conjunction with the accompanying drawings as follows.

Figure 1:
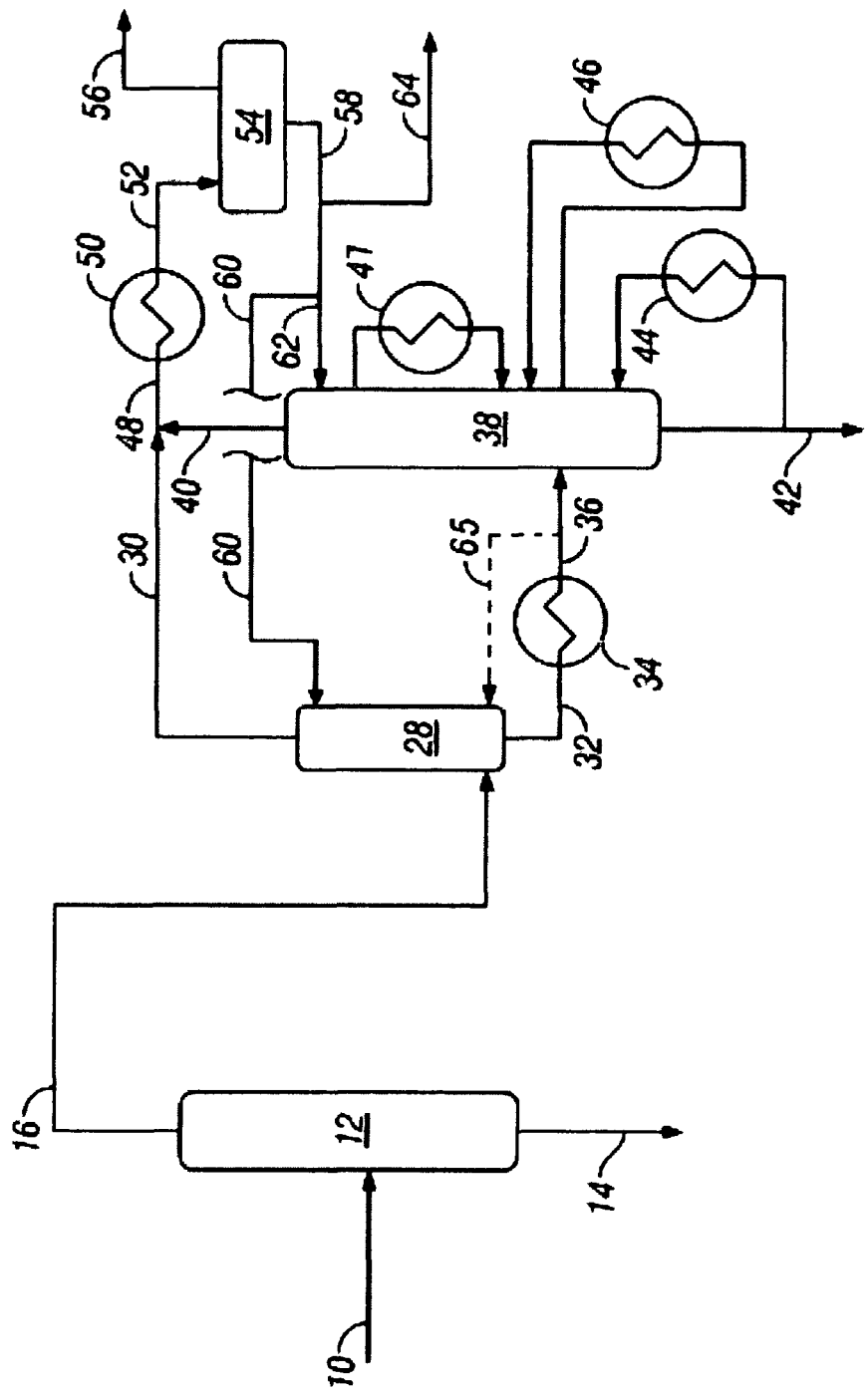
FIG. 1 depicts a simplified flow diagram of one example embodiment to increase the capacity of an olefin recovery process.

The embodiments are detailed below with reference to the listed Figures.

DETAILED DESCRIPTION OF THE EMBODIMENTS

Before explaining the embodiments in detail, it is to be understood that the embodiments are not limited to the particular embodiments and that they can be practiced or carried out in various ways.

The embodiments relate to processes to separate light hydrocarbons and methods to increase the capacity of the C2-splitter while maintaining or improving the quality of the ethane-ethylene separation.

In one embodiment, a process to separate a light hydrocarbon stream comprising ethylene, ethane, and C3+ hydrocarbons into an ethylene stream, an ethane stream, and a C3+ hydrocarbon stream, can include feeding the light hydrocarbon stream to a deethanizer; separating the light hydrocarbons in the deethanizer to form a C3+ hydrocarbon bottoms stream and a C2-rich overhead stream comprising ethylene and ethane; separating the C2-rich stream in a C2-rectifier to form a first ethylene stream and an ethane-rich bottoms stream; and separating the ethane-rich bottoms stream in a C2-splitter to form a second ethylene stream and an ethane stream.

In one embodiment, the C2-rich overhead stream from a deethanizer can include acetylene. When acetylene is present, the processes can include recovering the acetylene in an acetylene recovery unit to form an acetylene stream and a stream lean in acetylene or essentially free of acetylene, e.g. having an acetylene content of less than 10 ppmv (parts per million on a volume basis); and feeding the stream comprising ethane and ethylene to the C2-rectifier. When acetylene is present, the processes can include contacting the C2-rich overhead stream with hydrogen in an acetylene converter unit to convert the acetylene to ethane and ethylene to form a stream lean in or essentially free of acetylene; and feeding the acetylene-lean or -free stream to the C2-rectifier.

The light hydrocarbon stream fed to the embodied processes can be a product stream from a depropanizer, a demethanizer, a debutanizer, a demethanizer stripper, a cracker furnace effluent, a catalytic reactor effluent, or a combination thereof.

The first ethylene stream can have greater than about 95 mole percent ethylene. Other examples of contents of the first ethylene stream include one or more of the following: greater than about 99.5 mole percent ethylene; greater than about 99.8 mole percent ethylene; greater than about 99.9 mole percent ethylene; or greater than about 99.95 mole percent ethylene.

The second ethylene stream can have greater than 95 mole percent ethylene. Other examples of contents of the second ethylene stream include one or more of the following: greater than about 99.5 mole percent ethylene; greater than about 99.8 mole percent ethylene; greater than about 99.9 mole percent ethylene; or greater than about 99.95 mole percent ethylene.

The embodiments relate to methods to retrofit processes to separate light hydrocarbons comprising operation of a deethanizer to separate the light hydrocarbons into a C3+ hydrocarbon bottoms stream and a C2-rich overheads stream comprising ethylene and ethane, and operation of a C2-splitter to separate the C2-rich overheads into an ethylene stream and an ethane stream, wherein the ethylene is condensed and collected in a C2-splitter overheads condensation system. The retrofit can include: installing a C2-rectifier to separate the C2-rich overheads stream from the deethanizer into a first ethylene stream and an ethane-rich stream; installing a line to transmit the C2-rich overheads stream to the C2-rectifier; and installing a line to transmit the ethane-rich stream from the C2-rectifier to the C2-splitter.

The methods can include: installing a line to transmit the first ethylene stream to the C2-splitter overheads condensation system, and installing a line to transmit reflux from the C2-splitter overheads condensation system to the C2-rectifier.

Alternatively, the methods can include: installing a C2-rectifier overheads condensation system to condense and collect the ethylene in the first ethylene stream and to supply reflux to the C2-rectifier. In another embodiment, the method can include: installing a line to transmit a C2-rectifier overhead stream to the C2-splitter overheads condensation system; installing a line to transmit reflux from the C2-splitter overheads condensation system to the C2-rectifier; and installing a line to collect the first ethylene stream as a side-draw from the C2-rectifier.

The embodied processes can increase the capacity of an ethane-ethylene separation system while maintaining a high purity separation.

With reference to the figures, FIG. 1 depicts a simplified flow diagram of one example embodiment to increase the capacity of an olefin recovery process. One or more hydrocarbon streams 10, such as an overhead stream from a depropanizer, a bottoms stream from a demethanizer, or a stream from a demethanizer stripper, for example, can be fed to deethanizer 12. In a deethanizer-first olefin recovery, a cracker furnace effluent can be fed to deethanizer 12. Deethanizer 12 can separate the light hydrocarbons into a bottoms stream 14 comprising C3's and heavier hydrocarbons and an overhead stream 16 comprising C2 hydrocarbons, including ethylene and ethane. Deethanizer 12 can include reboilers, condensers, pumps, control valves, and other typical processing equipment that are standard in the industry.

Overhead stream 16 can be fed to a bottom tray of C2-rectifier 28 to form ethylene stream 30 and an ethane-rich bottoms stream 32. A "rectifier" as used herein is understood to mean a fractional distillation zone wherein vapor from a feed stream is contacted with liquid relatively lean in ethane so that the overhead ethylene stream is ethane-lean, and usually does not provide for reboiling or stripping of ethylene from the liquid collected from the feed tray. Ethane-rich bottoms stream 32 can be heated or cooled as necessary in heat exchanger 34, and fed in line 36 to C2-splitter 38. C2-splitter 38 can separate ethane-ethylene stream 36 into an overhead ethylene stream 40 and ethane stream 42. A portion of ethane-ethylene stream 36 can be fed to C2-rectifier 28 via line 65. C2-splitter 38 can include one or more reboilers 44, 46, one or more side condensers 47 and can also include pumps, drums, control valves, and other typical processing equipment that are standard in the industry.

Overhead ethylene stream 40 and ethylene stream 30 can be collected in ethylene stream 48 and chilled in heat exchanger 50 to form chilled ethylene stream 52. Chilled ethylene stream 52 can be fed to condensate drum 54, where the ethylene liquid can be collected and any vapor can be removed as stream 56. The collected ethylene can be recovered in line 58, a portion of which can supply ethylene to lines 60, 62 to reflux C2-rectifier 28 and C2-splitter 38, respectively, and the remainder recovered in ethylene product stream 64.

Figure 2:
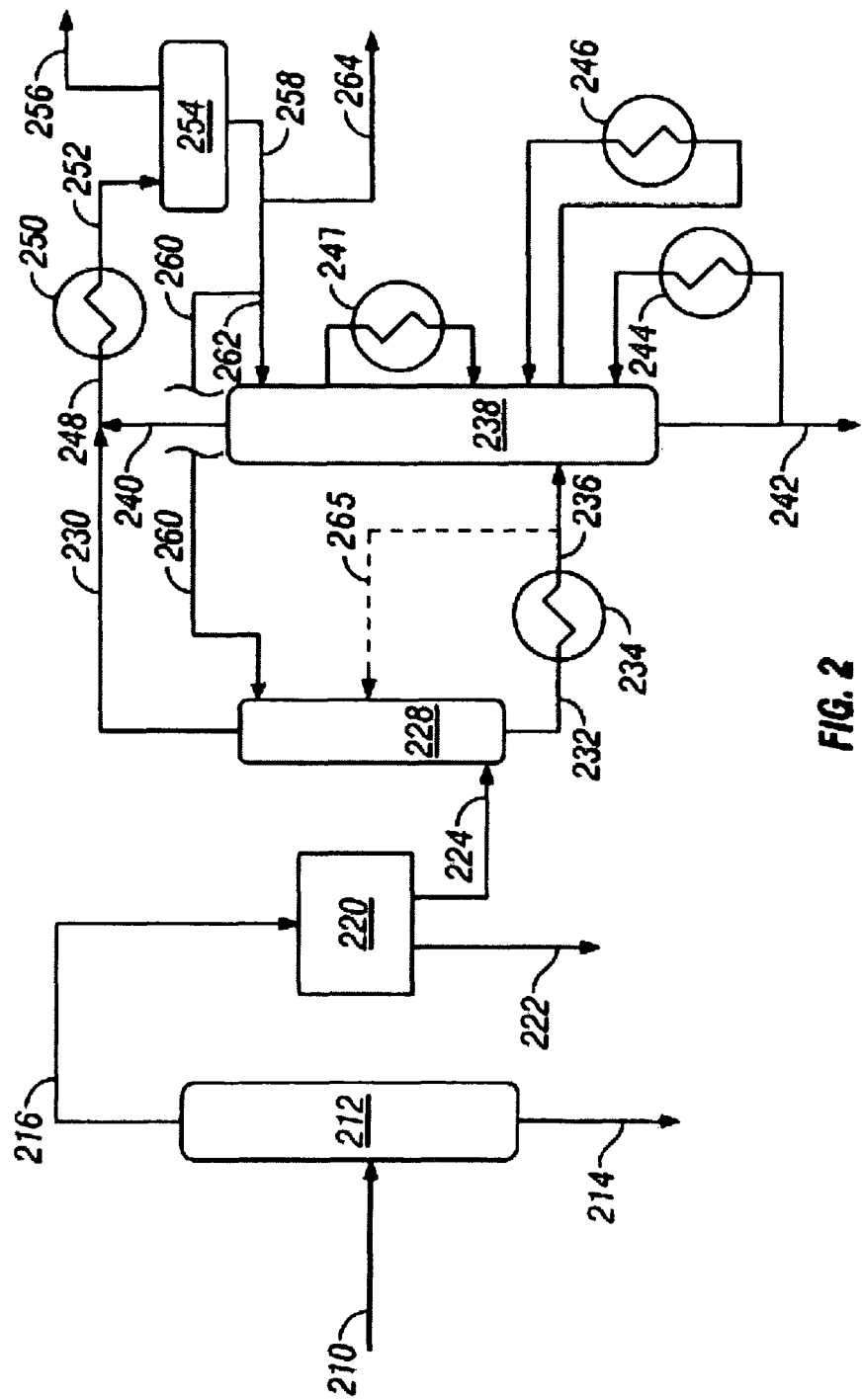
FIG. 2 depicts a simplified flow diagram of one example embodiment to increase the capacity of an olefin recovery process, where the olefin recovery process includes an acetylene separation unit.
Figure 3:
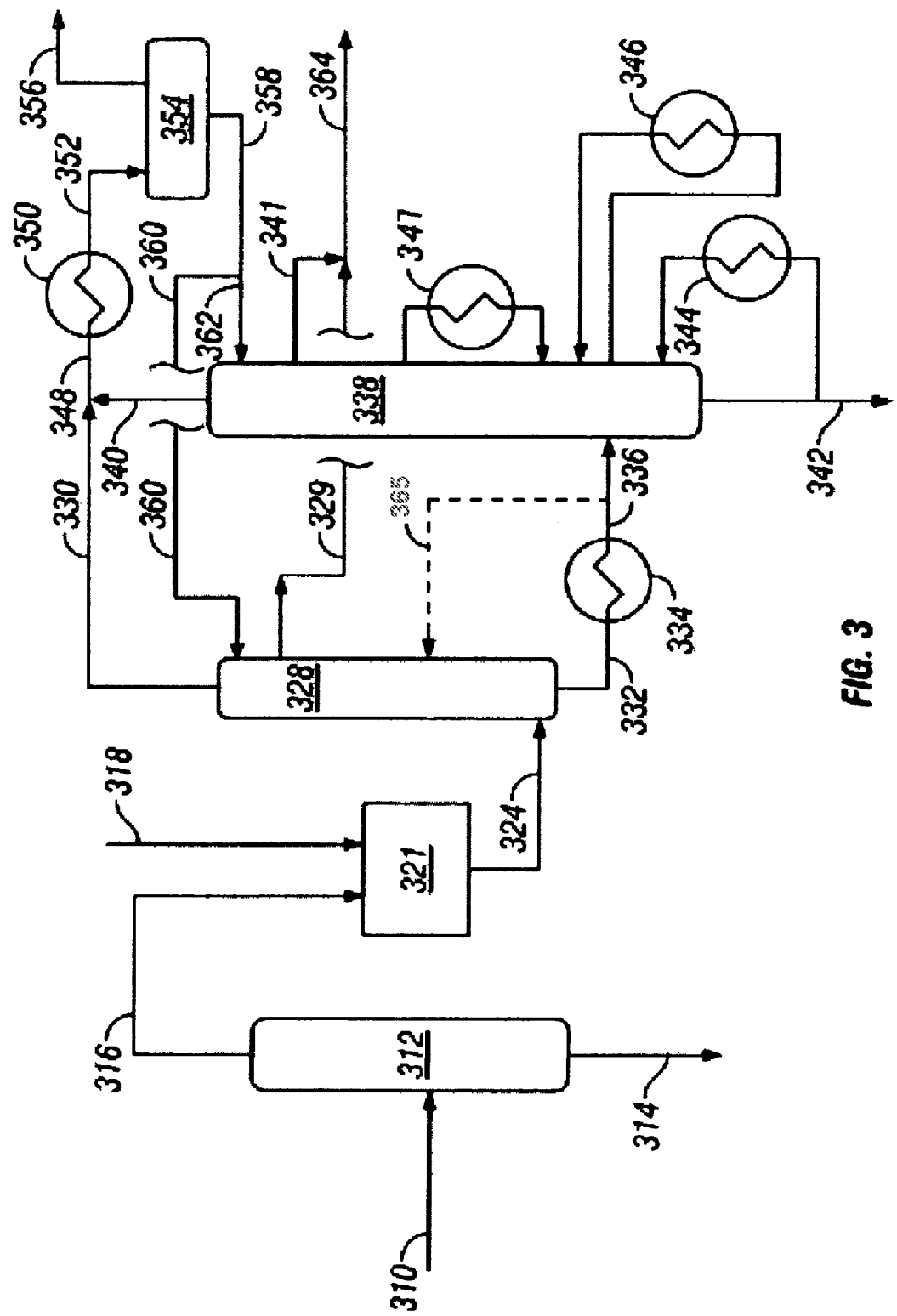
FIG. 3 depicts a simplified flow diagram of one example embodiment to increase the capacity of an olefin recovery process, where the olefin recovery process includes an acetylene conversion unit.

Other example embodiments to increase the capacity of an ethane-ethylene separation system are illustrated in FIG. 2 and FIG. 3, where the feed stream or streams to the deethanizer can comprise ethane, ethylene, acetylene, and C3+ hydrocarbons, such as, for example, in a demethanizer-first scheme. When acetylene is present, the C2 overhead stream from the deethanizer can be processed to recover the acetylene in an acetylene recovery unit, or alternatively, the acetylene can be reacted with hydrogen to form ethane and propane in an acetylene converter unit.

FIG. 2 depicts a simplified flow diagram of one example embodiment to increase the capacity of an olefin recovery process, where the olefin recovery process includes an acetylene separation unit. One or more light hydrocarbon streams 210, such as an overhead stream from a depropanizer, a bottoms stream from a demethanizer, or a stream from a demethanizer stripper for example, can be fed to deethanizer 212. Deethanizer 212 can separate the light hydrocarbons into a bottoms stream 214 comprising C3's and heavier hydrocarbons and an overhead stream 216 comprising C2 hydrocarbons, including acetylene, ethylene and ethane. Deethanizer 212 can include reboilers, condensers, pumps, control valves, and other typical processing equipment that are standard in the industry.

Overhead stream 216 can be fed to an acetylene recovery unit 220, which can separate the acetylene from the ethane and ethylene, forming acetylene stream 222 and ethane-ethylene stream 224 lean in acetylene. Ethane-ethylene stream 224 can be fed to C2-rectifier 228 to form ethylene stream 230 and an ethane-rich bottoms stream 232. Ethane-rich bottoms stream 232 can be heated or cooled as necessary in heat exchanger 234, and fed in line 236 to C2-splitter 238. C2-splitter 238 can separate ethane-ethylene stream 236 into an overhead ethylene stream 240 and bottoms ethane stream 242. A portion of ethane-ethylene stream 236 can be fed to C2-rectifier 228 via line 265. C2-splitter 238 can include one or more reboilers 244, 246, one or more side condensers 247 and can also include pumps, drums, control valves, and other typical processing equipment that are standard in the industry.

Overhead ethylene stream 240 can be combined with rectifier overhead ethylene stream 230. Combined ethylene stream 248 can be chilled in heat exchanger 250 forming vapor-liquid stream 252. Vapor-liquid stream 252 can be fed to condensate drum 254, where the ethylene liquid can be collected and any vapor can be removed as stream 256. The ethylene can be recovered in line 258, a portion of which can supply ethylene to lines 260, 262 to reflux C2-rectifier 228 and C2-splitter 238, respectively; the remainder of the ethylene collected in line 258 can be recovered in ethylene product stream 264.

FIG. 3 depicts a simplified flow diagram of one example embodiment to increase the capacity of an olefin recovery process, where the olefin recovery process includes an acetylene conversion unit. FIG. 3 examples a manner in which the separation process changes due to the presence of hydrogen in the feed stream sent to the ethane-ethylene separation system. One or more light hydrocarbon streams 310, such as a bottoms stream from a demethanizer, or a stream from a demethanizer stripper for example, can be fed to deethanizer 312. Deethanizer 312 can separate the light hydrocarbons into a bottoms stream 314 comprising C3's and heavier hydrocarbons and an overhead stream 316 comprising C2 hydrocarbons, including acetylene, ethylene and ethane. Deethanizer 312 can include reboilers, condensers, pumps, control valves, and other typical processing equipment that are standard in the industry.

Overhead stream 316 can be fed with hydrogen containing stream 318 to an acetylene converter unit 321 to react any acetylene with the hydrogen to form additional ethane and ethylene. Reactor effluent stream 324, lean in acetylene, can be fed to C2-rectifier 328 to form ethylene stream 329 as a side draw, overhead vapor stream 330 containing most of the unreacted hydrogen fed to acetylene converter unit 321, and an ethane-rich bottoms stream 332. Ethane-rich bottoms stream 332 can be heated or cooled as necessary in heat exchanger 334, and fed in line 336 to C2-splitter 338. C2-splitter 338 can separate ethane-ethylene stream 336 into an overhead stream 340, side-draw ethylene stream 341, and bottoms ethane stream 342. A portion of ethane-ethylene stream 336 can be fed to C2-rectifier 328 via line 365.

C2-splitter 338 can include one or more reboilers 344, 346, one or more side condensers 347 and can also include pumps, drums, control valves, and other typical processing equipment that are standard in the industry.

Overhead stream 340 can be collected with rectifier overhead stream 330 in stream 348 and chilled in heat exchanger 350 to form ethylene stream 352. Stream 352 can be fed to condensate drum 354, where the ethylene liquid can be collected and any vapor, including the unreacted or excess hydrogen, and inerts can be purged in purge stream 356. Liquid collected in drum 354 can be recovered in line 358, which can supply liquid to lines 360, 362 to reflux C2-rectifier 328 and C2-splitter 338, respectively. Ethylene side-draw 341 can be collected with C2-rectifier 328 side-draw 329 to form ethylene product stream 364.

In describing the example processes illustrated in the figures, the rectifier has been illustrated as being integrated with the condensate system of the C2-stripper. An independent condensate system can be used for the rectifier, if needed for additional capacity.

The processes described herein can be used to retrofit and increase the capacity of an ethylene-ethane separation system where the C2-splitter is capacity-limited. Retrofitting can be accomplished by installing a C2-rectifier; installing a line to route the deethanizer overheads (or acetylene converter effluent or acetylene separator effluent) to a bottom tray of the C2-rectifier; integrating the C2-rectifier overheads with the condensate system of the C2-splitter; and installing a line to transmit the C2-rectifier bottoms to a feed tray of the C2-splitter. Any additional heating or cooling requirements can be met by installing additional heat exchangers as necessary.

Example: A simulation of the process to increase the capacity of an ethane-ethylene separation system, where any acetylene is recovered in an acetylene recovery unit (similar to the embodiment exampled in FIG. 2), obtained the results presented in Table 1.

TABLE 1

| Stream/Unit | Temperature (° C.) | Pressure (kg/sq. cm) | Flow Rate (kg/h) | Duty (MM kcal/h) |
|---|---|---|---|---|
| 224 | −13.7 | 28.2 | 95852 | |
| 230 | −19.0 | 26.5 | 93870 | |
| 232 | −15.7 | 27 | 81145 | |
| 234 | | | | 5.62 |
| 240 | −20.5 | 25.5 | 338856 | |
| 242 | 3.0 | 26.7 | 12819 | |
| 244 | | | | 6.91 |
| 246 | | | 160000 | 11.4 |
| 250 | | | | −25.18 |
| 256 | −20.8 | 25.5 | 77133 | |
| 258 | −20.8 | 25.3 | 355593 | |
| 260 | −20.1 | 30.1 | 79164 | |
| 262 | −20.1 | 30.1 | 270529 | |
| 264 | −20.8 | 25.3 | 5900 | |

The C2-rectifier was simulated having 70 trays. The system with the rectifier resulted in simulated production of 99.98 mol % pure ethylene, with the rectifier capacity equal to 21.5% of the C2-splitter capacity. This result means that an increase in ethylene production capacity of the system is at least 21.5% greater than the use of the C2-splitter alone.

Other variations of the above disclosed process to increase the capacity of the C2-splitter accounting for particular separation schemes, such as demethanizer-first, deethanizer-first, depropanizer-first, and the like, should be readily apparent to those skilled in the art.

While these embodiments have been described with emphasis on the embodiments, it should be understood that within the scope of the appended claims, the embodiments might be practiced other than as specifically described herein.

What is claimed is:

1. A process to separate one or more light hydrocarbon streams comprising ethylene, ethane, and C3+ hydrocarbons into an ethylene stream, an ethane stream, and a C3+ hydrocarbon stream, comprising:
   feeding the one or more light hydrocarbon streams to a deethanizer;
   separating the light hydrocarbons in the deethanizer to form a C3+ hydrocarbon bottoms stream and a C2-rich overhead stream comprising ethylene and ethane;
   separating the C2-rich overhead stream in a C2-rectifier to form a first ethylene stream and an ethane-rich bottoms stream, wherein the C2-rectifier is operated without reboiling the ethylene introduced to the C2-rectifier;
   separating the ethane-rich bottoms stream in a C2-splitter to form a second ethylene stream and an ethane stream; and
   mixing the first ethylene stream and the second ethylene stream to form a combined ethylene stream.

2. The process of claim 1, wherein the C2-rich overhead stream further comprises acetylene, and the process further comprises
   recovering the acetylene in an acetylene recovery unit to form an acetylene stream and a stream lean in acetylene; and
   separating the stream lean in acetylene in the C2-rectifier to form the ethylene stream and the ethane-rich bottoms stream.

3. The process of claim 1 wherein the C2-rich overhead stream further comprises acetylene, the process further comprising:
   contacting the C2-rich overhead stream with a hydrogen rich stream in an acetylene converter unit to convert the acetylene to ethane and ethylene to form a stream lean in acetylene; and
   feeding the acetylene-lean stream to the C2-rectifier.

4. The process of claim 1 wherein the one or more light hydrocarbon streams comprise a product stream from a depropanizer, a demethanizer, a debutanizer, a demethanizer stripper, a cracker furnace effluent, or a combination thereof.

5. The process of claim 1 wherein the C2-splitter is fitted with a reboiler to further increase an amount of the second ethylene stream separated from the ethane-rich bottoms stream.

6. The process of claim 1, further comprising refluxing a portion of the ethylene as ethylene condensate to the C2-rectifier.

7. The process of claim 1, further comprising condensing the combined ethylene stream to provide an ethylene condensate and refluxing at least a portion of the ethylene condensate to the C2-splitter.

8. The process of claim 1, wherein the C2 rich overhead stream is introduced to the C2 rectifier as a vapor.

9. The process of claim 1, wherein the C2-rich overhead stream is introduced to the C2 rectifier at a location below a bottom tray of the C2 rectifier and wherein the C2 splitter comprises two reboilers and one side condenser.

10. A method to retrofit a process to separate light hydrocarbons comprising operation of a deethanizer to separate the light hydrocarbons into a C3+ hydrocarbon bottoms stream and a C2-rich overheads stream comprising ethylene and ethane, and a C2-splitter to separate the C2-rich overheads into an ethylene stream and an ethane stream, wherein the ethylene is condensed and collected in a C2-splitter overheads condensation system, and wherein the C2-splitter is capacity-limited, the method comprising:

installing a C2-rectifier to separate the C2-rich overheads stream from the deethanizer into a first ethylene stream and an ethane-rich stream, wherein the C2-rectifier is operated without reboiling the ethylene introduced to the C2-rectifier;

installing a line to transmit the C2-rich overheads stream to the C2-rectifier;

installing a line to transmit the ethane-rich stream from the C2-rectifier to the C2-splitter; and installing a line to transmit the first ethylene stream to the C2-splitter overheads condensation system such that the first ethylene stream mixes with the ethylene stream from the C2-splitter.

11. The method of claim 10 further comprising:
installing a line to transmit a reflux from the C2-splitter overheads condensation system to the C2-rectifier.

12. The method of claim 11 further comprising installing a C2-rectifier overheads condensation system to condense and collect the ethylene in the first ethylene stream and to supply reflux to the C2-rectifier.

13. The method of claim 10 further comprising:
installing a line to transmit reflux from the C2-splitter overheads condensation system to the C2-rectifier; and
installing a line to collect the first ethylene stream as a side-draw from the C2-rectifier.

14. The method of claim 10 wherein the process to separate light hydrocarbons further comprises operating an acetylene recovery unit.

15. The method of claim 10 wherein the C2-splitter is fitted with a reboiler to further increase an amount of the ethylene stream separated from the ethane-rich stream.

16. A method for olefin production, comprising:
separating one or more light hydrocarbon streams comprising ethylene, ethane, and one or more C3+ hydrocarbons into a C2 hydrocarbon-containing stream and a C3+ hydrocarbon-containing stream;
rectifying the C2 hydrocarbon-containing stream in a C2-rectifier into a first ethylene stream and an ethane-rich bottoms stream by contacting the C2 hydrocarbon-containing stream with a liquid, ethylene rich stream, wherein the C2-rectifier is operated without reboiling the ethylene introduced to the C2-rectifier;
separating the ethane-rich bottoms stream to form a second ethylene stream and an ethane stream;
mixing the first ethylene stream and the second ethylene stream to form a combined ethylene stream; and
condensing the combined ethylene stream to provide an ethylene condensate.

17. The method of claim 16, wherein rectifying the C2 hydrocarbon-containing stream into a first ethylene stream and an ethane-rich bottoms stream is performed in a rectifier wherein vapor from the C2 hydrocarbon-containing stream is contacted with the liquid of the liquid, ethylene rich stream.

18. The method of claim 16, wherein rectifying the C2 hydrocarbon-containing stream into a first ethylene stream and an ethane-rich bottoms stream is performed in a rectifier having a fractional distillation zone wherein vapor from the C2 hydrocarbon-containing stream is contacted with the liquid of the liquid, ethylene rich stream.

* * * * *